(12) United States Patent
Huang

(10) Patent No.: US 10,890,751 B2
(45) Date of Patent: Jan. 12, 2021

(54) SYSTEMS AND APPLICATIONS FOR GENERATING AUGMENTED REALITY IMAGES

(71) Applicant: Yu-Hsuan Huang, Taipei (TW)

(72) Inventor: Yu-Hsuan Huang, Taipei (TW)

(*) Notice: Subject to any disclaimer, the term of this patent is extended or adjusted under 35 U.S.C. 154(b) by 0 days.

(21) Appl. No.: 16/428,180

(22) Filed: May 31, 2019

(65) Prior Publication Data
US 2019/0285867 A1    Sep. 19, 2019

Related U.S. Application Data

(63) Continuation-in-part of application No. 15/420,122, filed on Jan. 31, 2017, now abandoned.

(30) Foreign Application Priority Data

Feb. 5, 2016 (TW) ............... 105104114 A

(51) Int. Cl.
*G02B 21/36* (2006.01)
*G02B 27/01* (2006.01)
(Continued)

(52) U.S. Cl.
CPC ....... *G02B 21/367* (2013.01); *G02B 27/0101* (2013.01); *G02B 27/0179* (2013.01);
(Continued)

(58) Field of Classification Search
CPC ......... G06T 19/006; G06T 2207/10056; A61B 2017/00207; A61B 2090/365;
(Continued)

(56) References Cited

U.S. PATENT DOCUMENTS 5,867,308 A    2/1999  Pensel et al.
6,147,797 A   11/2000  Lee
(Continued)

FOREIGN PATENT DOCUMENTS

CN    103340686 A    10/2013
JP    201153512 A    12/2011
(Continued)

OTHER PUBLICATIONS

Yu-Hsuan Huang et al; 2015. Scope+: a stereoscopic video see-through augmented reality microscope. In SIGGRAPH Asia 2015 Emerging Technologies (SA '15). Association for Computing Machinery, New York, NY, USA, Article 21, 1-3. DOI:https://doi.org/10.1145/2818466.2818476 (Year: 2015).*

*Primary Examiner* — John Villecco
(74) *Attorney, Agent, or Firm* — Muncy, Geissler, Olds & Lowe, P.C.

(57) ABSTRACT

The systems and applications for generating the augmented reality (AR) images are disclosed. The system includes a processing module and a digital microscope module having a plurality of camera units, and the processing module tracks and parses the user's motions to generate the related control signals, the virtual objects composed to form the AR images according to the received instant images of the observed objects captured by the digital microscope module. Moreover, the processing module generates and outputs the AR images composing of the instant images and the user interface (UI), icons, objects, video and/or information related to the interactive applications while the display mode switch or the real-time tutorial and sharing is triggered.

17 Claims, 21 Drawing Sheets

(51) Int. Cl.
*G06F 3/01* (2006.01)
*G09B 5/02* (2006.01)
*G09B 19/24* (2006.01)

(52) U.S. Cl.
CPC ............... *G06F 3/011* (2013.01); *G09B 5/02* (2013.01); *G09B 19/24* (2013.01); *G02B 2027/014* (2013.01); *G02B 2027/0134* (2013.01); *G02B 2027/0138* (2013.01); *G02B 2027/0141* (2013.01); *G02B 2027/0187* (2013.01)

(58) Field of Classification Search
CPC ...... H04N 13/239; G02B 21/18; G02B 21/20; G02B 21/22; G02B 21/36; G02B 21/365; G02B 21/367
See application file for complete search history.

(56) References Cited

U.S. PATENT DOCUMENTS

| | | | |
|---|---|---|---|
| 6,636,354 | B1 | 10/2003 | D'Hooge et al. |
| 7,262,907 | B2 | 8/2007 | Rentzsch |
| 8,358,338 | B2 | 1/2013 | Aizaki |
| 8,390,675 | B1 | 3/2013 | Riederer |
| 8,934,169 | B2 | 1/2015 | Mirlay |
| 8,976,238 | B2 | 3/2015 | Ernsperger et al. |
| 9,378,407 | B2 | 6/2016 | Zhang et al. |
| 9,835,841 | B2 | 12/2017 | Yang |
| 2001/0055062 | A1* | 12/2001 | Shioda ............... G02B 21/0012 348/79 |
| 2004/0070667 | A1 | 4/2004 | Ando |
| 2006/0028717 | A1 | 2/2006 | Dunn |
| 2007/0188603 | A1* | 8/2007 | Riederer ............... G02B 21/22 348/54 |
| 2013/0084012 | A1 | 4/2013 | Murphy et al. |
| 2013/0113894 | A1 | 5/2013 | Mirlay |
| 2013/0221218 | A1 | 8/2013 | Lee et al. |
| 2014/0160264 | A1* | 6/2014 | Taylor ............... G02B 21/008 348/79 |
| 2015/0022054 | A1 | 1/2015 | Monfray et al. |
| 2015/0084990 | A1 | 3/2015 | Laor |
| 2015/0173846 | A1 | 6/2015 | Schneider et al. |
| 2016/0364911 | A1 | 12/2016 | Jo et al. |
| 2017/0026634 | A1 | 1/2017 | Mirlay |
| 2017/0231714 | A1 | 8/2017 | Kosmecki et al. |
| 2017/0258529 | A1* | 9/2017 | Winne ............... A61B 34/20 |
| 2017/0336614 | A1 | 11/2017 | Mercer |
| 2017/0363854 | A1 | 12/2017 | Filippov |
| 2018/0014904 | A1 | 1/2018 | Yu et al. |
| 2018/0024341 | A1 | 1/2018 | Romanowski et al. |
| 2018/0125340 | A1 | 5/2018 | Ishikawa et al. |
| 2018/0188520 | A1 | 7/2018 | Hattori |
| 2018/0205932 | A1* | 7/2018 | Yu ............... G06T 11/60 |
| 2018/0256304 | A1 | 9/2018 | Sheena |
| 2019/0325785 | A1* | 10/2019 | Huang ............... G06T 19/006 |
| 2020/0097727 | A1* | 3/2020 | Stumpe ............... G02B 21/365 |

FOREIGN PATENT DOCUMENTS

| | | |
|---|---|---|
| TW | M482797 U | 7/2014 |
| TW | M528481 U | 9/2016 |

* cited by examiner

SYSTEMS AND APPLICATIONS FOR GENERATING AUGMENTED REALITY IMAGES

CROSS REFERENCE TO RELATED APPLICATION

This application is a continuation-in-part of U.S. application Ser. No. 15/420,122 filed on Jan. 31, 2017. The U.S. application Ser. No. 15/420,122 claims the benefit of Taiwan Patent Application Serial No. 105104114 filed on Feb. 5, 2016. The entirety of each said Application is incorporated herein by reference.

BACKGROUND OF THE INVENTION

1. Field of the Invention

The present application generally relates to the field of interaction systems and applications for a user and an observed object, and more particularly to a system and applications for generating and operating the augmented reality (AR) images.

2. Description of Related Art

Nowadays, the way to express the multimedia data through the stereo and dynamic augment reality (AR) images instead of the plat and static one is popular due to the higher processing ability of computer and the increasing demands on the visualization, straightforward operation, quality, response time and interaction. The AR technique is derived from that of the virtual reality (VR), and the major difference between them is that the VR creates the virtual environment or scenes and the virtual objects, whereas the AR creates and overlaps or composes the related virtual objects of real world's concrete or stereo objects into the images of the real world's environment or scenes and then displays on the whole. In other words, the user can receive and realize the real-time response, information, and the operation result of the concrete or stereo objects in the real world's environment or scenes. Accordingly, developing more system and method of interactive application with lower latency and alignment error is beneficial to the user.

Some known AR-based interactive applications adopt a marker-based, a non-marker-based, an optical see-through based, or a video see-through method for image processing. Specifically, a marker-based AR application detects the marker which can be recognized by the computer in the AR images and then retrieves and composes the AR contexts or information to the images of the real world's environment or scenes. However, the interaction and the applications are restricted due to the requirements such as the exact size, continuous boundary and specific pattern of the marker. On the other hand, a non-marker AR application detects visually distinctive features distributed in the AR image, compares it with a preset static data stored in a feature database and then composes and display when they are matched. In general, the marker-based and the non-marker method lack of the stereo effect to the dynamic or multimedia data.

The optical see-through method utilizes a translucent reflection mirror to exhibit the real world's and the virtual environment, images and objects, whereas the video see-through method composes the virtual images to the image sequence of the real world's environment captured by the camera. The disadvantage of using the former technique is that it has the alignment error and the display latency due to the asynchronous in the real and the virtual images during the display-timing, and the reduction of the luminance resulted from the translucent reflection mirror. In other hands, the disadvantage of using the latter technique is that it has the display latency when displaying the images to the user, although it has no alignment error and the display latency since it's synchronous during display-timing.

Moreover, for the user operating the traditional electronic or optical microscope, the disadvantage of using that is he/she shall move his/her head, eyes or hands away from the microscope for looking up some references from the book, manual or computer and recording the experimental results repeatedly, and the lacks of the interactive instructions or guidance in the forms of text, graphic, image or video stream, evaluating or sharing mechanism and the remote control may result in the inconvenience, inefficiency, and interruption frequently. In addition, the lacks of supporting the operation or practice using the real tools or instruments rather than a specimen or a prosthesis to the real objects such as the body or the tissue of an organism is one possible cause to lower the learner's motivation. Therefore, a need exists for a system and a method that can provide high quality and reliable stereo AR images.

SUMMARY OF THE INVENTION

One of the objectives of the present invention is to provide a system for generating the AR images to solve the problem caused by lacks of the interaction and then improve or enhance the technique that of the traditional microscope device.

One of the objectives of the present invention is to provide another system for generating the AR images to solve the problem caused by lacks of the interaction and then improve or enhance the technique that of the traditional microscope device.

One of the objectives of the present invention is to provide a method for generating the AR images of an observed object to extend the fields or types of the AR applications.

One of the objectives of the present invention is to provide a microsurgery training system applying a stereoscopic video see-through technique to extend the fields of the AR techniques and the interaction.

One of the objectives of the present invention is to provide an electronic component assembly training and examining system applying a stereoscopic video see-through technique to extend the fields of the AR techniques and the interaction.

One of the objectives of the present invention is to provide an interactive object observing system applying a stereoscopic video see-through technique to extend the fields of the AR techniques and the interaction.

One of the objectives of the present invention is to provide a non-transitory computer readable medium storing the programs, the software, the algorithm, or the firmware to improve the portability and integration.

One of the objectives of the present invention is to provide a computer application program using or installing in the system for generating the AR images.

One of the objectives of the present invention is to provide a system-on-chip (SoC) system to lower the cost of system establishment, simplify the control flow and achieve the system downsizing.

One of the objectives of the present invention is to provide a digital microscope module that can be installed to a system for generating the augmented reality (AR) images.

In order to achieve the objectives, a preferred embodiment of the system for generating the augmented reality (AR)

images of the present invention includes a processing module and a digital microscope module having a vergence module and a plurality of camera units capturing an instant image of an observed object and transmitting to the processing module in response to a control signal. The observed object is tiny in its volume or mass and suitable to apply a microscopic or a vergence process by the function of the vergence module adjusting the corresponding or geometric relationship between a reflection mirror unit and the camera units in response to the control signals related to the user's motions or an automatic adjustment rule. The processing module configured to track and parse the user's motions to the observed object and generate the corresponding AR images, wherein if the user's motions includes a trigger of an interactive application including a switch of the display modes for the observed object or an activation of a real-time tutorial or sharing at least, the processing module further generates the AR images composed with/without a user interface (UI), icons, objects, video and/or information related to the interactive application respectively. Accordingly, the user can obtain good user experience due to the retrieval of the real-time feedback and interaction.

In some embodiments, the system further includes a single-chip microcontroller for activating the digital microscope module in response to the control signals, and a positioning module configured to couple to the digital microscope module having the vergence module including a vergence controller unit and the reflecting mirror unit for moving in an operable space in response to the control signals. In addition, the user's motions include that entering into or departing from the operable space by using a simulation tool, user's hand or finger or a real surgical or experimental instrument operated by the user, approaching, touching, leaving, operating, installing or fixing partial or all of the object and/or changing the status of the operating or feature region. Accordingly, the blurring issue resulted from the insufficient vergence to the tiny observed object is dismiss.

In some embodiments, the system further includes an operable interface module configured or coupled to the processing module for selecting or performing the user's motions by the user and/or configured to have a operating parameter adjustment object and/or a display mode switching object, wherein the user's motions further include temporarily remove, transparent or disable the real-time tutorial or sharing and the related AR images with/without virtual object for preventing the interference in response to a temporarily disable mechanism. Moreover, the operating parameter adjustment object configured is provided for the user to adjust the focus, the ratio to zoom-in/-out, the distance to shift, the angle to rotate or the parameter value of a light source of the digital microscope module, and the display mode switching object configured is provided for the user to select the single or simultaneous display or arrangement of the AR images of the same or different objects, and the display mode is selected from the group of a single, a parallel and an array mode. Furthermore, the system further includes an evaluating module and/or an error alerting configured to generate or output an evaluating result, an unalignment response or a tip for trigger operation correspondingly when the AR imaged generated by the processing module is satisfied or unsatisfied to a preset requirement, or includes a feedback or community module configured to store, transmit or share the AR images, the evaluating result, the unalignment response or the tip for trigger operation.

In order to achieve the objectives, another preferred embodiment of the system for generating the augmented reality (AR) images of the present invention includes a processing module and a digital microscope module. The processing module configured to track and parse the user's motions, generate the corresponding control signals, receive the instant images having at least one object or the status of at least one operating or feature region that were retrieved in response to the user's motions or the control signals, process the instant images to generate at least one virtual object and the AR images overlapped with the virtual object, and wherein if the user's motions includes a trigger of an interactive application including a switch of the display modes for the object or an activation of a real-time tutorial or sharing at least, the processing module further generates the instant images transparent, solid or dynamic in part or on the whole, that of the interactive application is triggered or the AR images composed with or without a user interface (UI), icons, objects, video and/or information related to the interactive application before or after the overlapping, invoking or displaying respectively. In addition, the digital microscope module configured to comprise a vergence module and a plurality of camera units at least, wherein the camera units capture the instant images in response to the control signals and then transmit to the processing module, the object is tiny in its volume or mass and suitable to apply a microscopic or a vergence process for observing and interacting, and the vergence module adjust the corresponding or geometric relationship between a reflection mirror unit and the camera units in response to the control signals or an automatic adjustment rule.

In order to achieve the objective, a preferred embodiment of the method for generating the augmented reality (AR) images of an observed object which is tiny in the volume or mass and suitable to apply a microscopic and a vergence process of the present invention includes the steps of: tracking and parsing the user's motions to generate the corresponding control signals, wherein the user's motions includes a trigger of an interactive application including a switch of the display modes for the object or an activation of a real-time tutorial or sharing at least; generating and processing the instant images of the observed object which is processed in transparent, solid or dynamic in part or on the whole or that of the status of the operating or feature region after an interactive application is triggered to form at least one virtual object; and generating the AR images composed with an user interface (UI), icons, objects, video, information related to the interactive application and the virtual object before or after the overlapping, invoking or displaying respectively.

In some embodiments, the user's motions includes operating a positioning module, a simulation tool, user's hand or finger or a real surgical or experimental instrument to enter into or depart from an operable space, approach, touch, leave, operate, install or fix partial or all of the object or all of the object and/or change the status of the operating or feature region; removing, transparentizing or disabling a real-time tutorial or sharing and the related AR images with/without the virtual object temporarily for preventing the interference in response to a temporary disable mechanism; and adjusting the focus, the ratio to zoom-in/-out, the distance to shift, the angle to rotate or the parameter value of a light source of the digital microscope module. Moreover, if the interactive application is a display mode switching, the method further includes the steps of: switching a display mode to a single, a parallel and an array mode to generate a single or simultaneous display or arrangement of the AR images of the same or different objects, and displaying the AR images to a display module configured as a head-mounted display (HMD), stereo display or a flat display. Accordingly, the method of the present invention improves the effect and smoothness due to the prevention of the blocking of line of sight by tracking and predicting the user's motions and processing such as removing temporarily or changing the virtual object to transparent, solid or dynamic in part or on the whole or that of the status of the operating or feature region after an interactive application is triggered to form at least one virtual object.

In order to achieve the objective, the microsurgery training system applying a stereoscopic video see-through technique, configuring the system for generating the augmented reality (AR) images of the present invention, is disclosed. The observed object is the real body or tissues of a tiny organism, a specimen or a prosthesis, and the stereoscopic video see-through technique is the technique that the digital microscope module captures the instant images of the observed object or the status of one of the operating or feature regions for the processing module to form, overlap and output the virtual object to a display module synchronously for diminishing the alignment error or reducing the latency. On the other hand, the microsurgery training system can be used to perform the method for generating the augmented reality (AR) images of an observed object of the present invention as well.

In order to achieve the objective, the electronic component assembly training and examining system applying a stereoscopic video see-through technique, configuring the system for generating the augmented reality (AR) images of the present invention, is disclosed. The observed objects is a circuit board for installing or fixing the electronic component, a medium or an electrical device, and the stereoscopic video see-through technique is the technique that the digital microscope module captures the instant images of the observed object or the status of one of the operating or feature regions for the processing module to form, overlap and output the virtual object to a display module synchronously for diminishing the alignment error or reducing the latency. On the other hand, the microsurgery training system can be used to perform the method for generating the augmented reality (AR) images of an observed object of the present invention as well.

In order to achieve the objective, the interactive object observing system applying a stereoscopic video see-through technique, configuring the system for generating the augmented reality (AR) images of the present invention, is disclosed. The observed objects is selected from the group of a tiny organism, a plant, a mineral, or an organic matter, an inorganic matter, a chemical element or a chemical compound, and the stereoscopic video see-through technique is the technique that the digital microscope module captures the instant images of the observed object or the status of one of the operating or feature regions for the processing module to form, overlap and output the virtual object to a display module synchronously for diminishing the alignment error or reducing the latency. On the other hand, the microsurgery training system can be used to perform the method for generating the augmented reality (AR) images of an observed object of the present invention as well.

In order to achieve the objective, the non-transitory computer readable medium storing the programs or firmware, wherein the programs or firmware loaded or assembly control or drive a system for generating the augmented reality (AR) images of the present invention, is disclosed. The programs or firmware controls the digital microscope module and generates the AR images.

In order to achieve the objective, the system-on-chip (SoC) system, configuring a processing module of the system for generating the augmented reality (AR) images of the present invention, is disclosed.

In order to achieve the objective, the digital microscope module, coupled or connected to the processing module of the system for generating the augmented reality (AR) images of the present invention, a computer host or a portable electronic device configured, connected or coupled to the processing module.

In some embodiments, the parts of a vergence module of the digital microscope module is a beam splitting element for the camera units to receive the instant images having at least one object or the status of at least one operating or feature region induced and then reflected by the beam splitting element.

In another embodiment, the digital microscope module includes the beam splitting element configured between the vergence module and the camera units for the camera units to receive the instant images having at least one object or the status of at least one operating or feature region reflected, induced and then reflected again to the beam splitting element by the vergence module.

BRIEF DESCRIPTION OF THE DRAWINGS

The aforementioned implementations of the present application, as well as additional implementations, will be more clearly understood as a result of the following detailed description of the various aspects of the application when taken in conjunction with the drawings.

DETAILED DESCRIPTION OF THE PREFERRED EMBODIMENT

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

To promote an understanding of the objectives, technical solutions, and advantages of the present application, embodiments of the present application are further described in detail below with reference to the accompanying drawings.

Figure 1A:
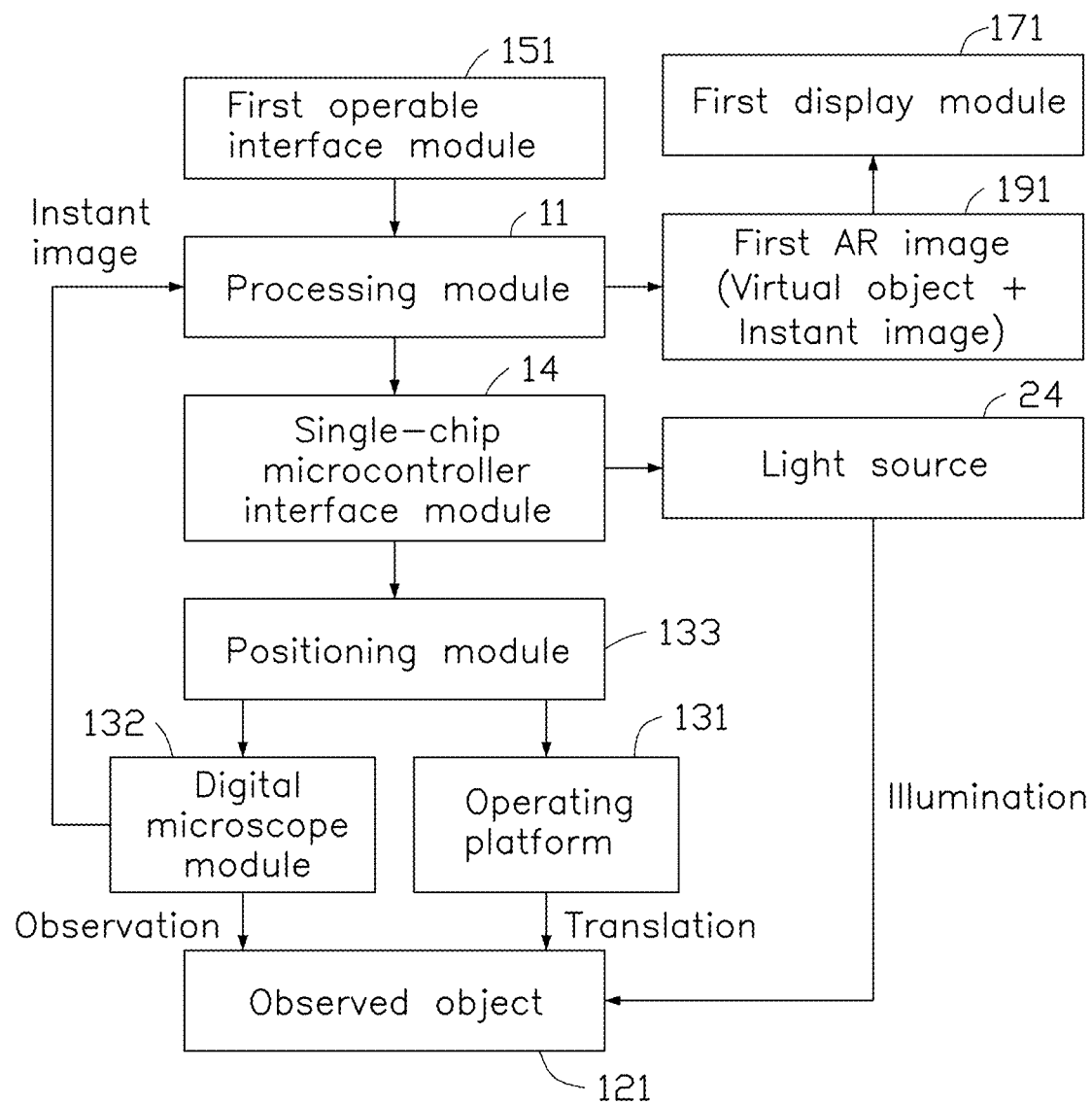
FIGS. 1A and 1B are system functional block diagrams illustrating the system for generating the AR images in accordance with the preferred embodiment of the present invention.
Figure 1B:
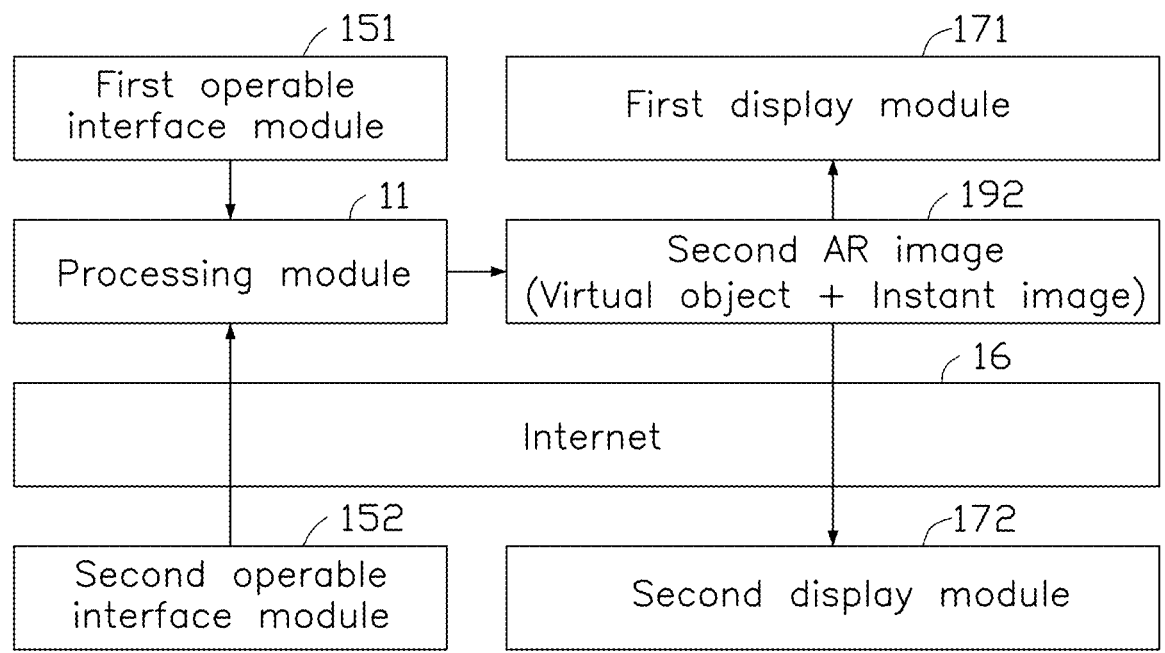

FIGS. 1A and 1B are system functional block diagrams illustrating the system for generating the AR images in accordance with the preferred embodiment of the present invention. As shown in FIG. 1A, the system for generating the AR images includes a processing module 11 coupled or connected to a computer host or a portable electronic device, a positioning module 133, an operating platform 131, a digital microscope module 132, a single-chip microcontroller interface module 14, a first operable interface module 151, a first display module 171, a light source 24, a first AR image 191, and an observed object 121. Another configuration of the system for generating AR images is shown in FIG. 1B. Preferably, the system in FIG. 1B allows a user to operate the present invention without being on the same location with the first operable interface module 151. The system in FIG. 1B includes the processing module 11, a second operable interface module 152, the first display module 171, a second display module 172, a second AR image 192, and an internet connection 16. Moreover, the computer host and the portable electronic device may be either coupled or connected to the first display module 171 for displaying the first AR image 191, or coupled or connected to the second display module 172 via the internet connection 16 for displaying the second AR image 192. The first display module 171 and the second display module 172 may be a head-mounted display (HMD), s stereo display, or a flat display for displaying the AR images or the stereo images. The second display module 172 and the second operable interface module 152 may be coupled or connected to a terminal having the calculating ability or a server for remote control. The single-chip microcontroller interface module 14 may be coupled or connected to the processing module 11 or between the processing module 11 and the digital microscope module 132. The single-chip microcontroller interface module 14 receives one or more control signals from the first operable interface module 151, receives one or more control signals from the processing module 11, or delivers any of the above control signals to the positioning module 133 to facilitate the movement of the digital microscope module 132. The single-chip microcontroller interface module 14 can be commercially available single-board computers, comprising Arduino, Rasberry Pi, Intel Edison, NVIDIA Tegra K1, NVIDIA Jetson TK1, or the like. Preferably, the single-chip microcontroller interface module 14 is Arduino. The positioning module 133, an operating platform 131 and the digital microscope module 132 can be coupled, connected or assembled together. The operating platform 131 provides a space for a user to place the real body or tissues of a tiny organism such as a butterfly in the embodiment, a specimen, a prosthesis, a circuit board, a medium or an electronic device as an observed object 121 to be observed. The positioning module 133 may be a mechanism or one or more mechanical structures for moving the digital microscope module 132, in response to the control signals issued by the single-chip microcontroller interface module 14, the computer host, or the portable electronic device. The positioning module 133 comprises one or more mechanical structures for moving the digital microscope module 132 in X-Y plane, X-Z plane, and Y-Z plane. The mechanical structure can be a motor, a screw, a gear, a belt, or the combination thereof. Preferably, the positioning module 133 is a motor module comprising a motor, a screw, and a belt.

Figure 2:
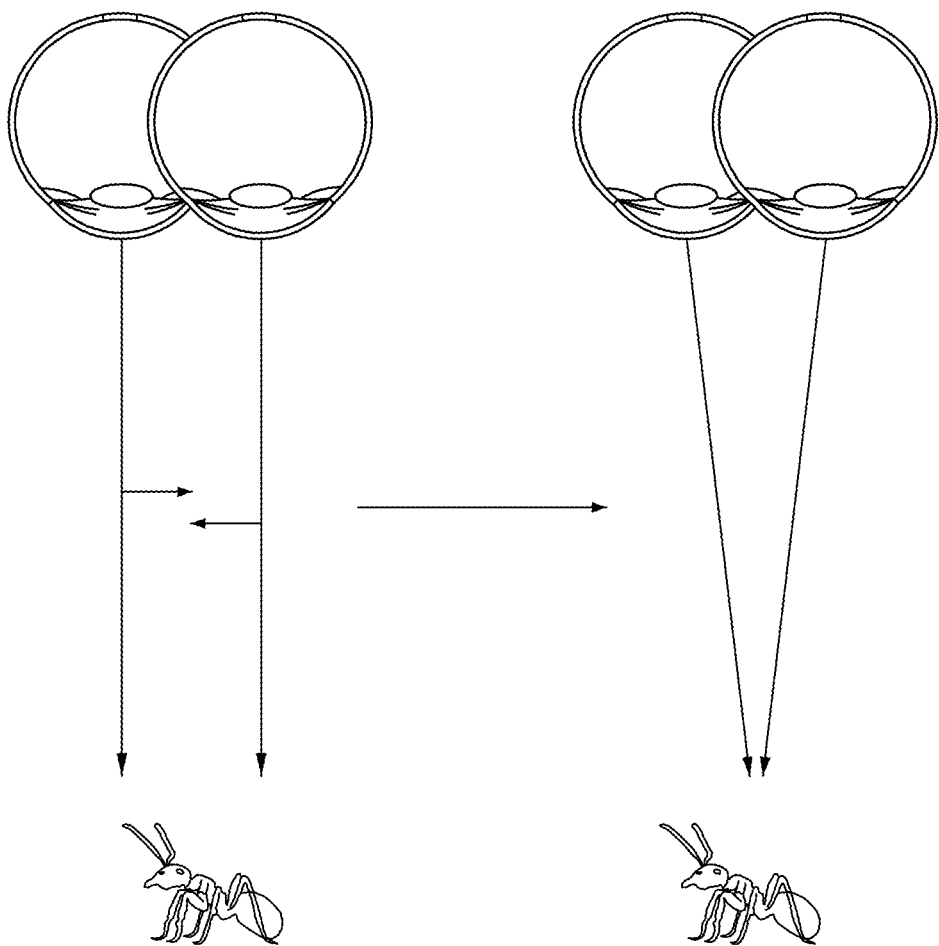
FIG. 2 is a schematic diagram illustrating the concept of vergence of the system for generating the AR images in accordance with the preferred embodiment of the present invention.
Figure 3:
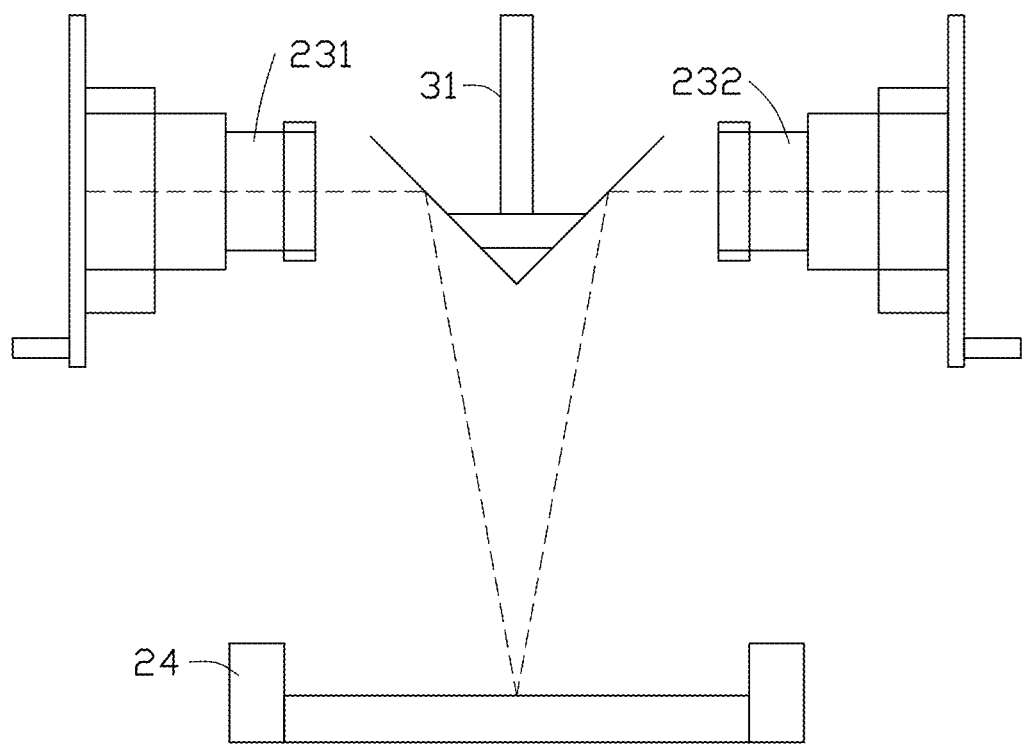
FIG. 3 is a block diagram illustrating the microscope module and the light source module of the system for generating the AR images in accordance with the preferred embodiment of the present invention.
Figure 4A:
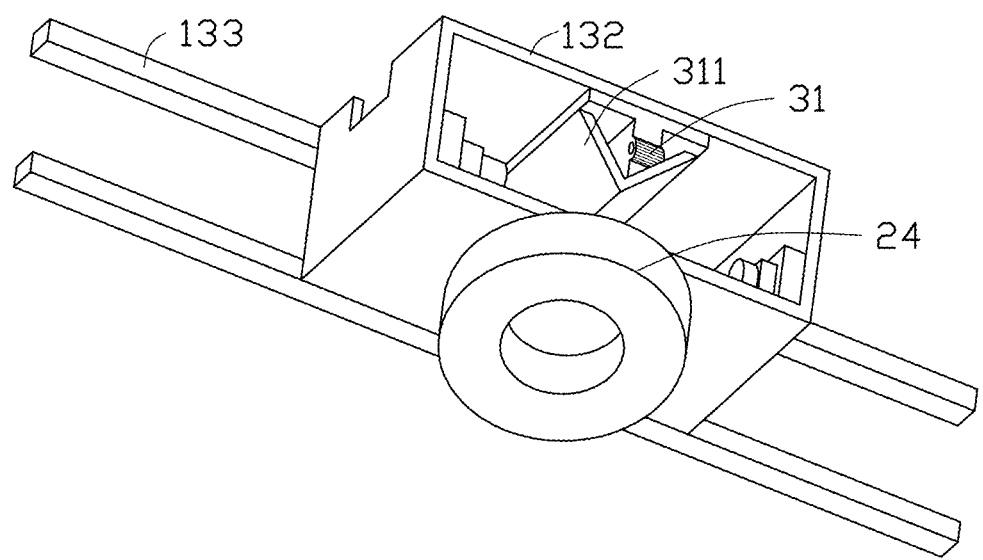
FIG. 4A is a block diagram illustrating the microscope module, the positioning module and the light source module of the system for generating the AR images in accordance with the preferred embodiment of the present invention.

FIG. 2 is a schematic diagram illustrating the concept of vergence of the system for generating the AR images in accordance with the preferred embodiment of the present invention. FIG. 3 is a block diagram illustrating the digital microscope module 132 and the light source module 24 of the system for generating the AR images in accordance with the preferred embodiment of the present invention. FIG. 4A is a block diagram illustrating the digital microscope module 132, the positioning module 133 and the light source module 24 of the system for generating the AR images in accordance with the preferred embodiment of the present invention. As shown in the left side of FIG. 2, it depicts the issue of interpupillary distance of imaging for a user to observe the tiny object such as an ant, and it can be fixed by adjusting either or both line of sight of the camera in the vergence process as shown in the right side of FIG. 2. The embodiments shown in FIGS. 1A, 1B, 3 and 4A depicts that the digital microscope module 132 includes two camera unit 231 and 232 capturing the instant image of the observed object which is tiny in its volume or mass and suitable to apply a microscopic and a vergence process performed by a vergence module 31 in response to the control signals related to the user's motions or an automatic adjustment rule.

Figure 4B:
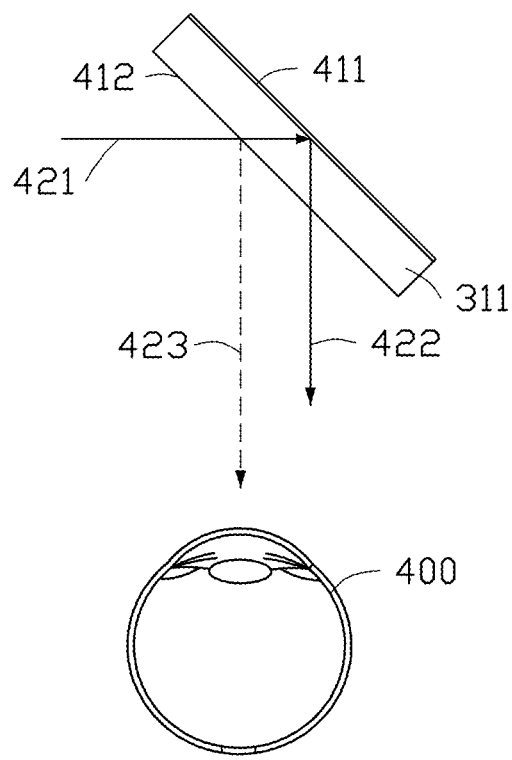
FIG. 4B is a schematic diagram illustrating a conventional reflection mirror.
Figure 4C:
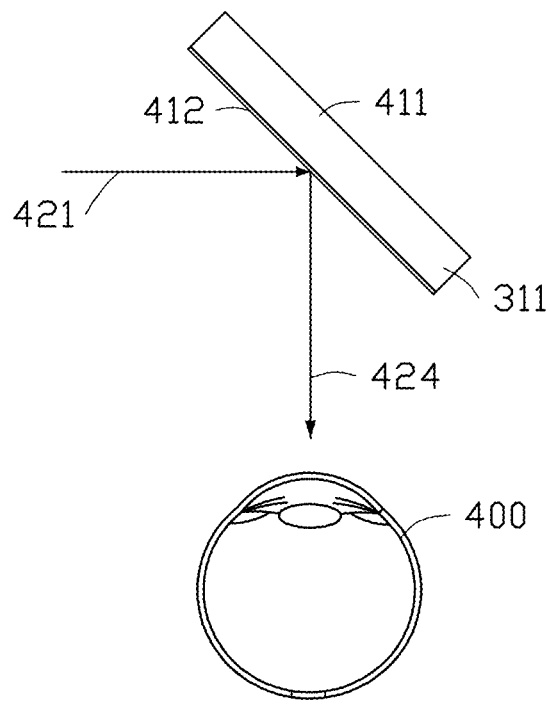
FIG. 4C is a schematic diagram illustrating the reflection mirror of the system for generating the AR images in accordance with the different preferred embodiments of the present invention.

FIGS. 4B and 4C are the schematic diagrams illustrating the reflection mirror unit 311 of the system for generating the AR images in accordance with the different preferred embodiments of the present invention. As shown in FIGS. 4B and 4C, a first side 411 and a second side 412 are two independent faces of the reflection mirror unit 311, wherein the reflection mirror unit 311 can be a glass or a transparent acrylic sheet. A reflection coating on the reflection mirror unit 311 can either be coated onto the first side 411 (as shown in FIG. 4B) or the second side 412 (as shown in FIG. 4C), to control the lights 422-424 projected to a user's eye 400. In FIG. 4B, the reflection coating is on the first side 411, and an incident light 421 is reflected by the reflection coating on the first side 411 to form a reflected light 422. The reflected light 422 is then projected into the user's eye 400. However, the second side 412 of the reflection mirror unit 311 may also reflect a portion of the incident light 421, thus forming a reflected light 423. Therefore, the user's eye may receive the reflected lights 422 and 423. The overlapped reflected lights 422 and 423 may cause irritation of eyesight or blurred images for the user.

In FIG. 4C, the reflection coating is on the second side 412 of the reflection mirror unit 311, and the incident light 421 is reflected by the reflection coating on the second side 412 to form a reflected light 424. The reflected light 424 is then projected into the user's eye 400. Because there are no undesired reflected lights, FIG. 4C is a preferred configuration for the present invention. The reflection coating on the second side 412 forms clear images with sharp edges.

Figure 4D:
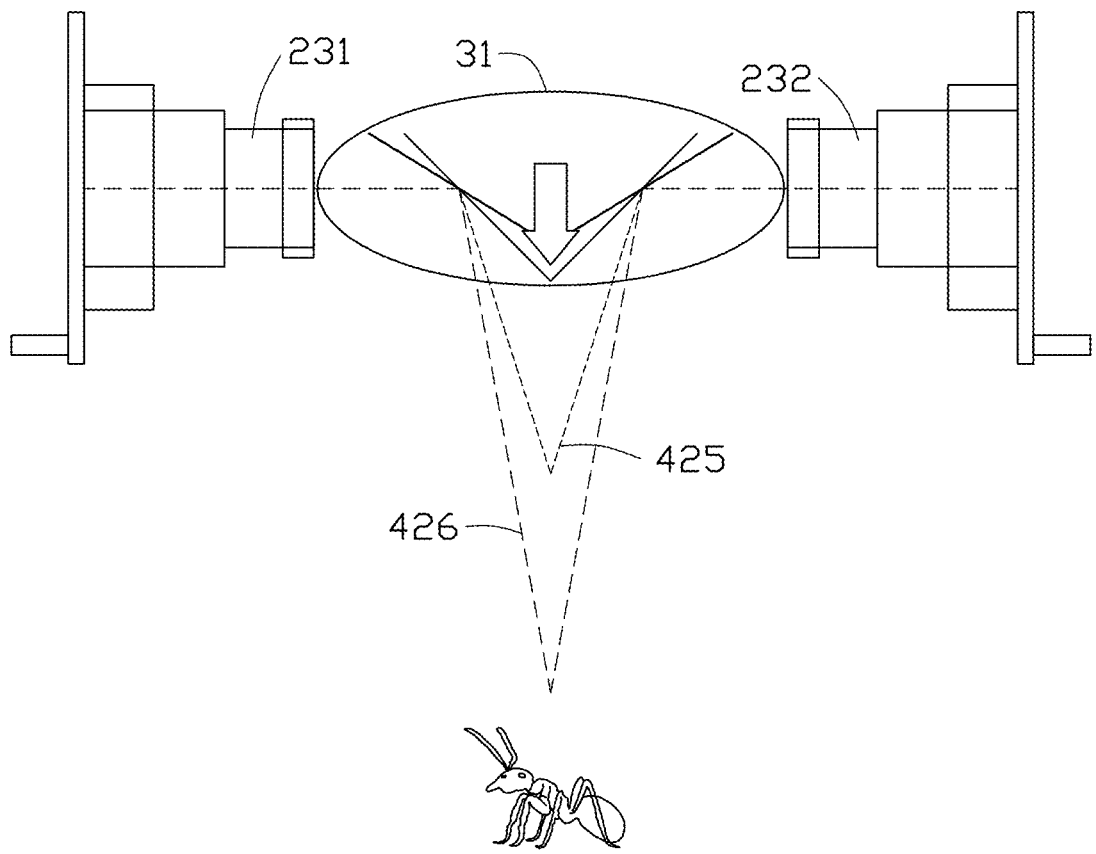
FIGS. 4D-4F are the schematic diagrams illustrating the vergence module, the beam splitting element and the beam splitting of the digital microscope module in accordance with the different preferred embodiments of the present invention.
Figure 4E:
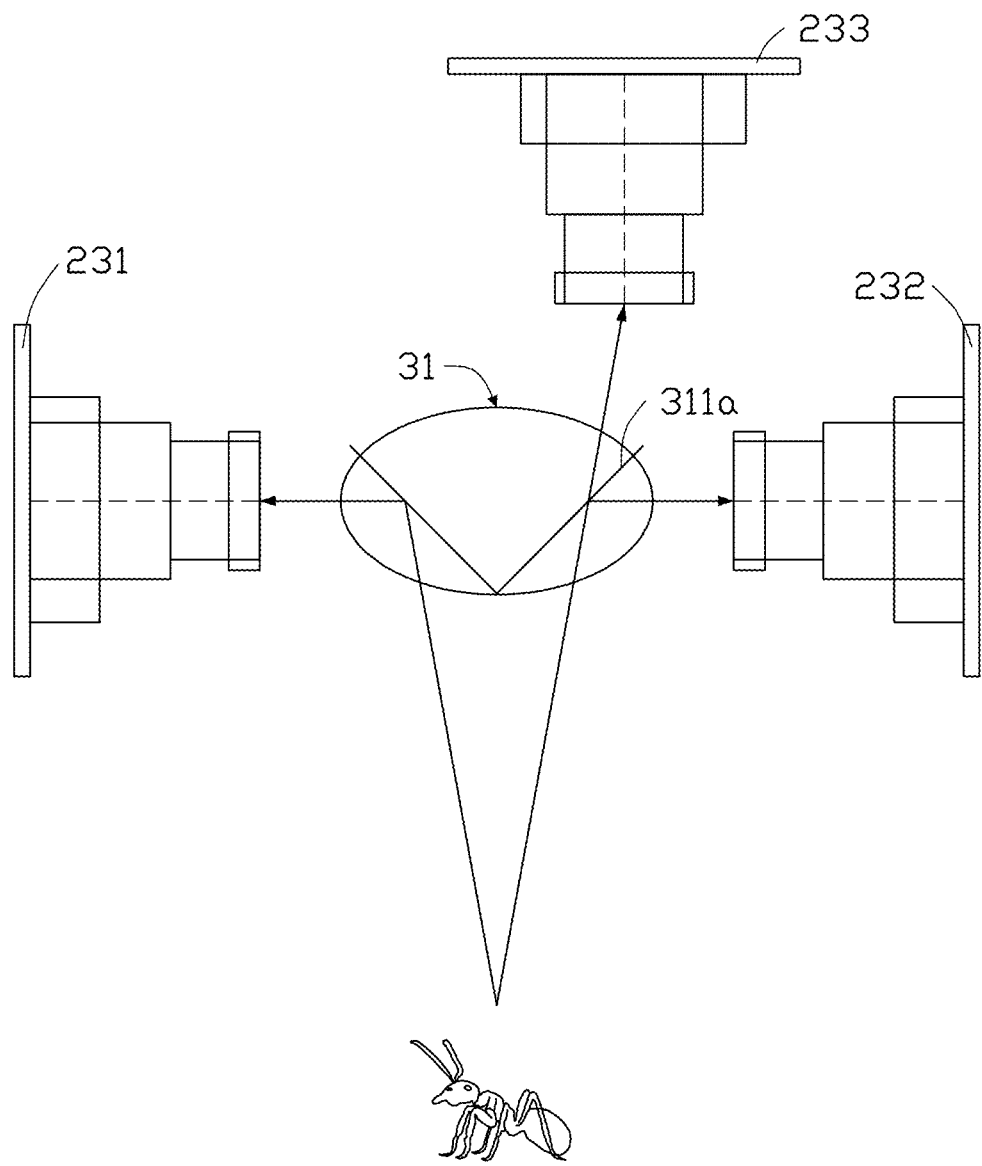
Figure 4F:
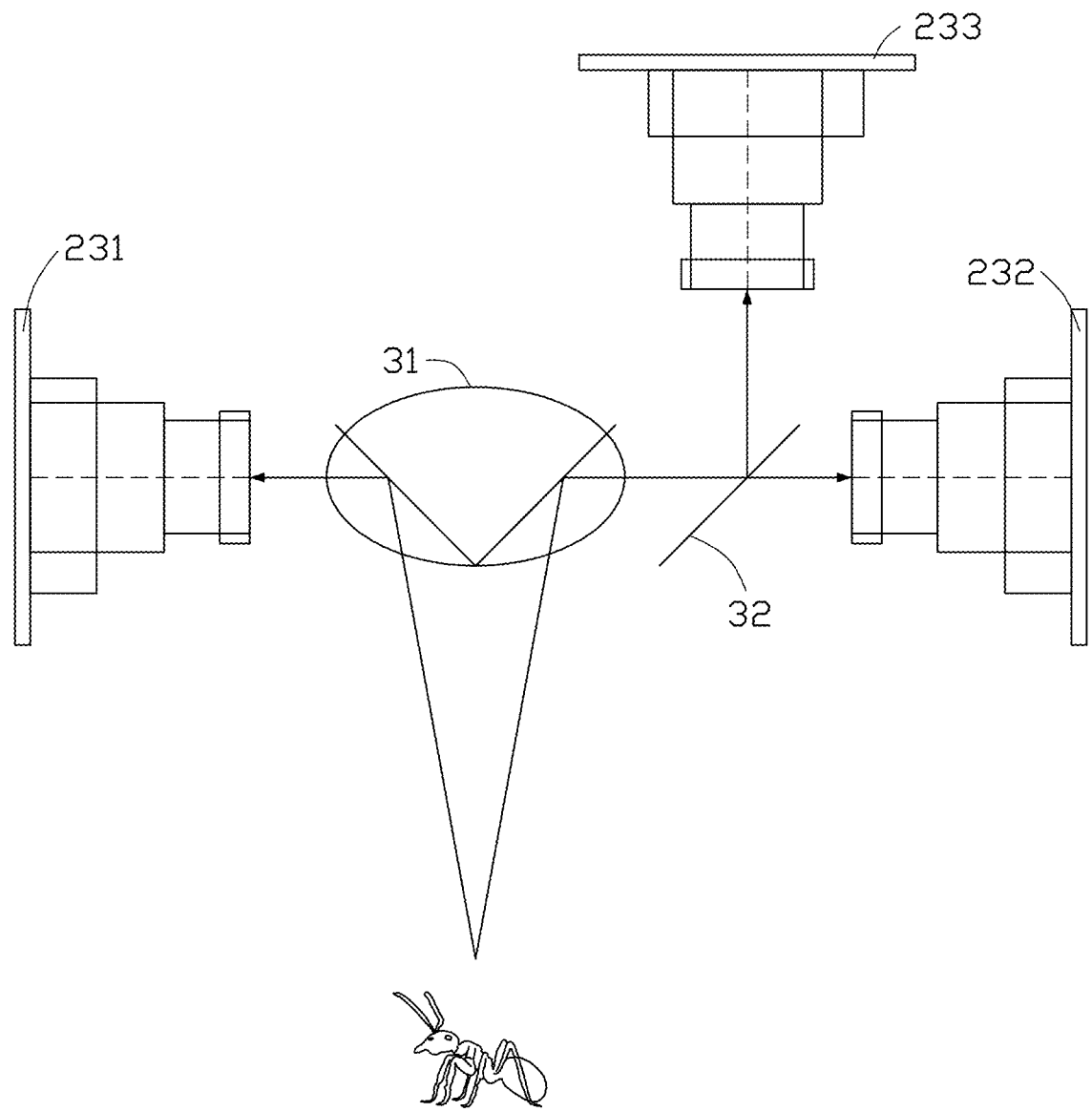

FIGS. 4D-4F are the schematic diagrams illustrating the vergence module 31, the beam splitting element 311a and the operation of beam splitting of the digital microscope module 132 in accordance with the different preferred embodiments of the present invention. Referring to FIGS. 4A-4F, the vergence module 31 includes a vergence controller unit adjusting the corresponding or geometric relationship between the reflection mirror unit 311 and the camera unit 231 and 232 in response to the control signals related to the user's motions or an automatic adjustment rule. The reflection mirror unit 311 with V-shaped in the embodiment is operatively regulated and/or adjusted to move in an operable space in response to the control signal. Additionally, materials, functions, or mechanisms may vary for adjusting the relationship between the reflection mirror unit 311 and the camera units 231 and 232, such as using a hinge. The circular light source 24 with LED 241 is set for preventing the shadow. In FIGS. 4D-4F, the location of the camera unit 231-233 is adjustable in response to different types of the vergence module 31. In addition, as shown in FIGS. 4D-4F, by observing the factors such as the reflection path, distance, inducing path, the light and the image 425 and 426, the design of capturing system or module affects the quality of the instant images and the AR images significantly.

FIGS. 4E and 4F are the schematic diagrams illustrating the vergence module 31, the beam splitting element 311a and the operation of beam splitting of the digital microscope module 132 in accordance with the different preferred embodiments of the present invention. In FIG. 4E, the vergence module 31 comprises a first beam splitting element 311a. Incident light is split into two lights by the first beam splitting element 311a, and the camera units 232 and 233 received the split lights respectively. In FIG. 4F, the digital microscope module 132 further comprises a second beam splitting element 32. The second beam splitting element 32 receives reflected light from the vergence module 31, and the reflected light from the vergence module 31 is split into two lights, and the camera units 232 and 233 received the split lights respectively.

Figure 5:
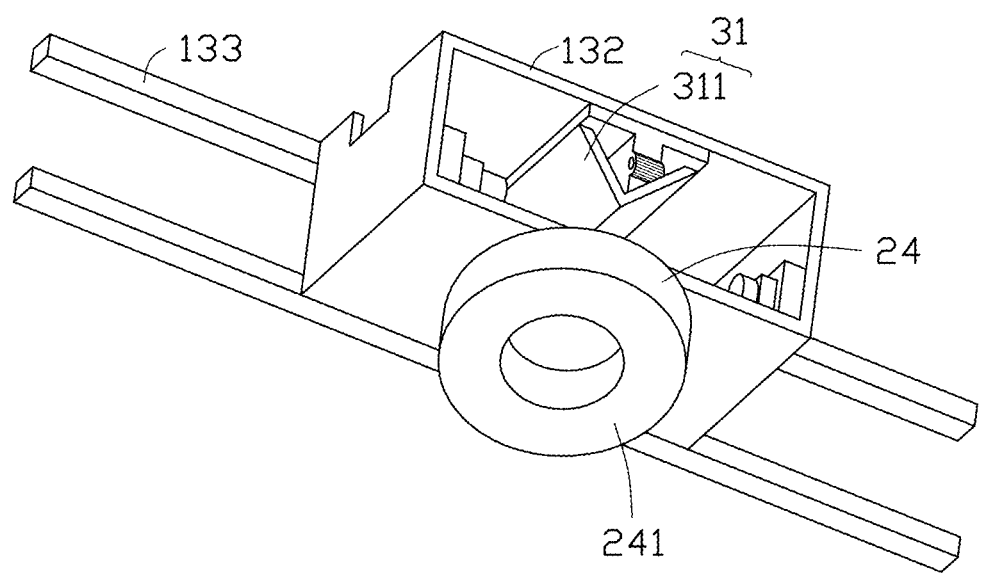
FIG. 5 is a schematic diagram illustrating the microscope module, the vergence module, the positioning module and the light source module of the system for generating the AR images in accordance with the preferred embodiment of the present invention.

FIG. 5 is a schematic diagram of the digital microscope module 132, the vergence module 31, the positioning module 133, and the light source 24, in accordance with the embodiments of the present invention. The digital microscope module 132, the vergence module 31, and the light source 24 are coupled to the positioning module 133.

Figure 6A:
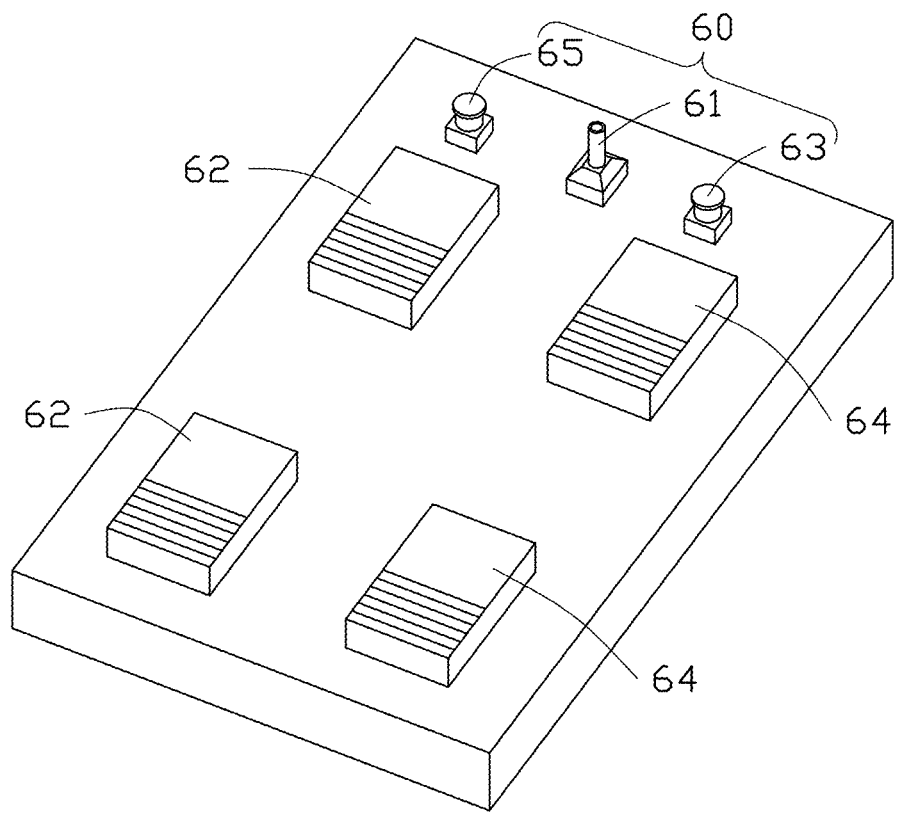
FIGS. 6A and 6B are the block diagrams illustrating the operable interface module and the simulation tool of the system for generating the AR images in accordance with the different preferred embodiments of the present invention.
Figure 6B:
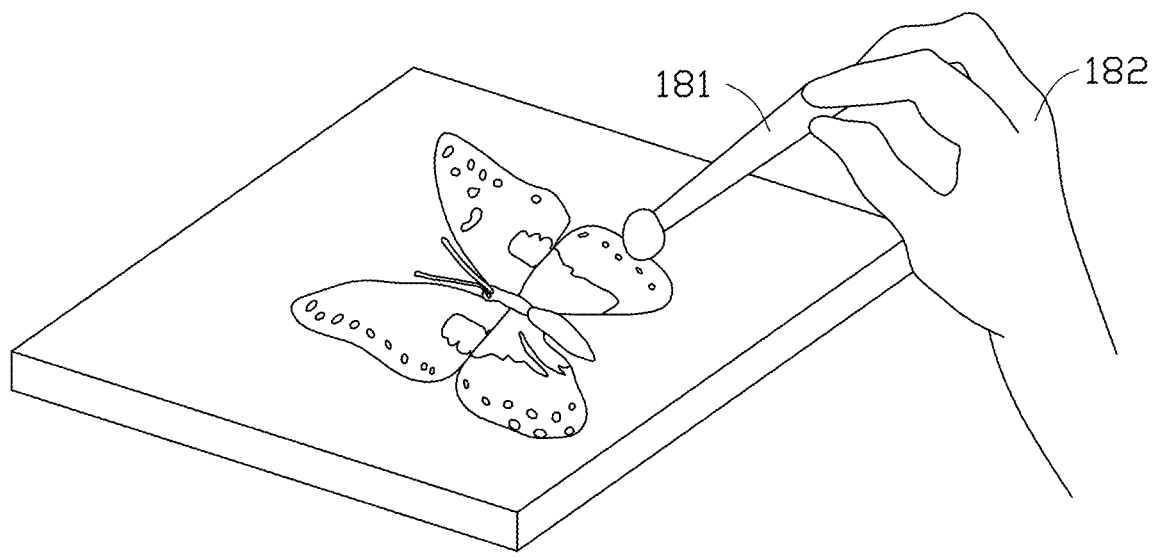
Figure 7:
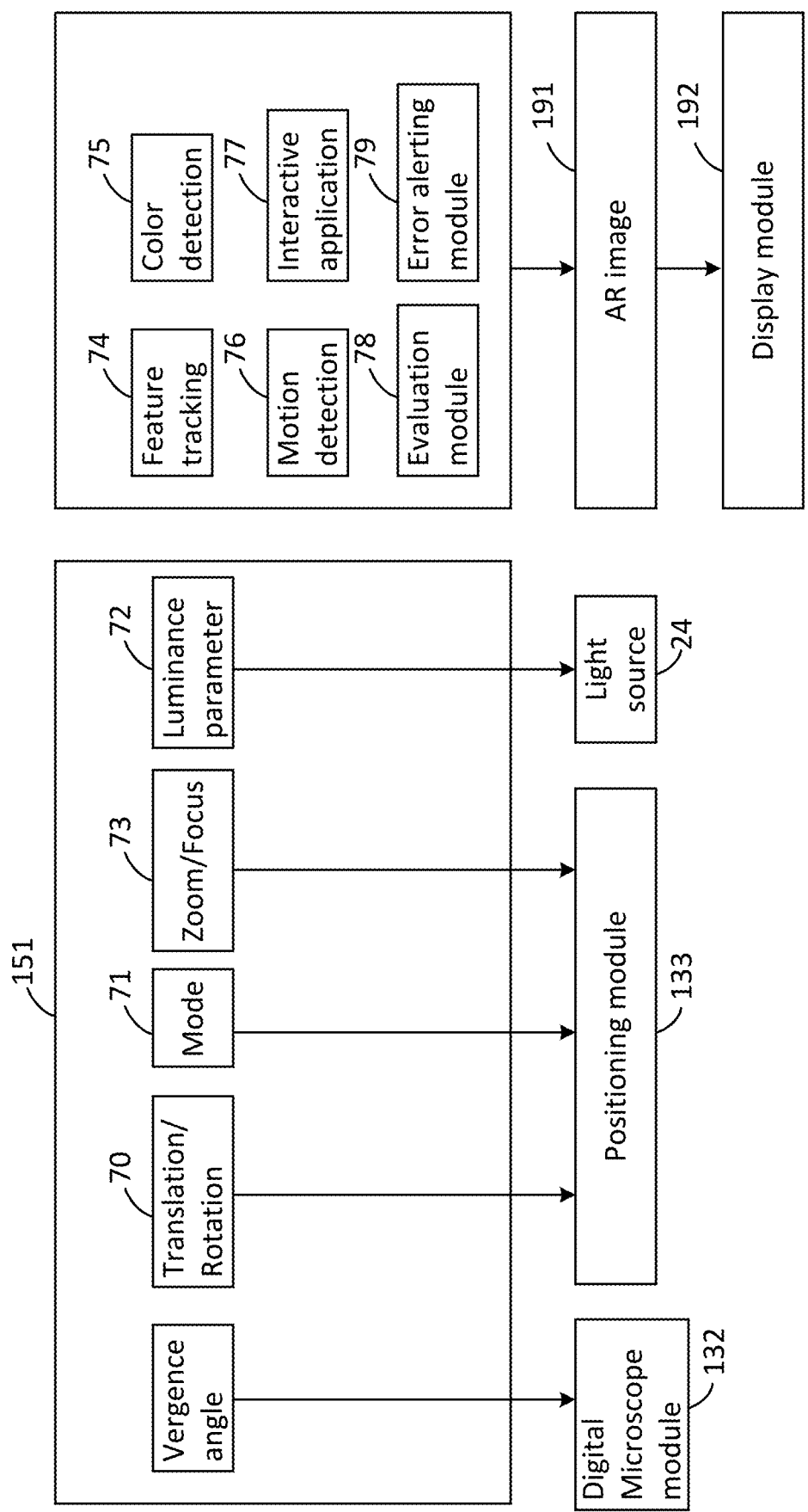
FIG. 7 is a flowchart illustrating the performing of function of the processing module of the system for generating the AR images in accordance with the preferred embodiment of the present invention.

FIGS. 6A and 6B are the block diagrams illustrating the simulation tool 181 and user's hand or finger 182 of the system for generating the AR images in accordance with the different preferred embodiments of the present invention, and FIG. 7 is a flowchart illustrating the performing of the function of the processing module 11 of the system for generating the AR images 191 in accordance with the preferred embodiment of the present invention. The processing module 11 is configured to track and parse the motions commands or instructions from the user via the first operable interface module 151. The processing module 11 can be a microprocessor with digital signal processor (DSP), a microprocessor without DSP, a coprocessor, a multi-core processor, a controller, a processing circuitry, a computer, an integrated circuit (IC), a graphics processing unit (GPU), a central processing unit (CPU), or a combination thereof. Preferably, the processing module 11 is a combination of a graphics processing unit (GPU) and a central processing unit (CPU). The user may instruct the first operable interface module 151 to generate the corresponding control signals to the light source 24 or the positioning module 133. The processing module 11 receives the instant images having at least one object or the status of at least one operating or feature region that was retrieved or captured by the digital microscope module 132, the instant image is then processed by the processing module 11 to perform an image feature tracking 74, color detection 75, motion detection 76 in response to the user's motions or the control signals. The processing module 11 processes the instant images to generate at least one virtual object and the AR image 191 and 192 overlapped with the virtual object to the display module 171. In addition, the user's motions includes the types of: operating a simulation tool 181, user's hand or finger 182 or a real surgical or experimental instrument (not shown in the FIGs) to enter into or depart from an operable space, approach, touch, leave, operate, install or fix partial or all of the object or all of the object and/or change the status of the operating or feature region. Moreover, If the user's motions includes a trigger of an interactive application 77 including a switch of the display modes for the object or an activation of a real-time tutorial or sharing, the processing module 11 further generates the instant images which are transparent, solid or dynamic in part or on the whole, that of the interactive application is triggered or the AR images composed with or without a user interface (UI), icons, objects, video and/or information related to the interactive application before or after the overlapping, invoking or displaying respectively. Furthermore, the processing module 11 includes an evaluating module 78 and/or an error alerting module 79 configured to generate or output an evaluating result, an unalignment response such as a flash of light or beep or a tip for trigger operation correspondingly when the AR images generated by the processing module 11 is satisfied or unsatisfied to a preset requirement. The evaluating module 78 provides an assessment based on the user's motion: the evaluating module 78 compares the user's motions with the preset requirement, generates an evaluation result, and may provide responses to the user based on the user's motions. Based on the type of the evaluation result, the responses provided by the evaluating module 78 can be a score or a yes/no signal. The evaluating module 78 can be a software, a firmware, a program, or an algorithm being stored in a non-transitory computer-readable medium in or coupled to the processing module 11. The alerting module 79 visualizes the response provided by the evaluating module 78 and presents the response in real-time. Such visualization can be that a green signal indicates the user's motion is correct, and a red signal indicates the user's motion is not correct. The alerting module 79 can be a software, a firmware, a program, or an algorithm being stored in the non-transitory computer-readable medium in or coupled to the processing module 11. The processing module 11 may also include a feedback or community module configured to store, transmit or share the AR images, the evaluation result, the unalignment response or the tip for trigger operation. The feedback or community module may upload the AR images to a website or a server, or broadcast the AR images to other users in real-time. The feedback or community module can be a software, a firmware, a program, or an algorithm being stored in the non-transitory computer-readable medium in or coupled to the processing module 11.

The user may use the first operable interface module 151 to generate control signals in the system, the control signals can be delivered to the single-chip microcontroller interface module 14, and the single-chip microcontroller interface module 14 then instructs the movement of the positioning module 133 in response to control signals. The first operable interface module 151 can be one or more devices for the user to switch, press, hold, or step on. The first operable interface module 151 may comprise buttons, switches, foot pedals, hand-held controllers, touch panels, remote control units, joysticks, mobile devices, or a combination thereof. Preferably, the first operable interface module 151 may be a foot pedal set 60, as shown in FIG. 6A. The first operable interface module 151 is configured or coupled to the processing module 11 for the user to operate and interact with the system. The first operable interface module 151 or the foot pedal set 60 is configured to have a plurality of operating parameter adjustment object 61-64 and/or a display mode switching object 65. The user's motions may include temporarily remove, change to transparent or disable the real-time tutorial or sharing and the related AR images with/without the virtual object for preventing the interference in response to a temporarily disable mechanism. The operating parameter adjustment object 61-64 are configured for the user to adjust the translation/rotation 70 (that is, a distance to shift and an angle to rotate), the mode 71(that is, the single display mode, the parallel display mode, or the array display mode), the zoom/focus 73 (that is, the focus or the ratio to zoom-in/-out), or the luminance parameter 72 of the light source 24 of the digital microscope module 132. In FIG. 6A, the operating parameter adjustment object 61 is a joystick, the operating parameter adjustment objects 62 and 64 are pedals, and the display mode switching object 65 and the operating parameter adjustment object 63 are buttons. Nevertheless, the operating parameter adjustment objects 61-64 and the display mode switching object 65 can be other mechanical structures that can be manually switched, pressed, clicked, moved, or lifted by the user to change its physical status. The display mode switching object 65 is configured for the user to select display modes of the system or arrangement of the AR images of the same or different objects 122-125. The display mode of the system is selected from the group of a single, a parallel, and an array mode, as shown in FIG. 8C.

FIG. 7 is a flowchart illustrating the performing of the function of the processing module 11 of the system for generating the AR images in accordance with the preferred embodiment of the present invention. The method for generating the augmented reality (AR) images of an observed object, wherein the observed object is tiny in its volume or mass and suitable to apply a microscopic and a vergence process, the method comprising the steps of: tracking and parsing the user's motions to generate the corresponding control signals, wherein the user's motions includes a trigger of an interactive application including a switch of the display modes for the object or an activation of a real-time tutorial or sharing at least; generating and processing the instant images of the observed object which is processed to transparent, solid or dynamic in part or on the whole or that of the status of the operating or feature region after an interactive application is triggered to form at least one virtual object; and generating the AR images composed with an user interface (UI), icons, objects, video, information related to the interactive application and the virtual object before or after the overlapping, invoking or displaying respectively. Moreover, the user's motions includes of: operating a positioning module 133, a simulation tool 181, user's hand or finger 182 or a real surgical or experimental instrument to enter into or depart from an operable space, approach, touch, leave, operate, install or fix partial or all of the object or all of the object and/or change the status of the operating or feature region; removing, changing to transparent or disabling a real-time tutorial or sharing and the related AR images with/without the virtual object temporarily for preventing the interference in response to a temporary disable mechanism; and adjusting the focus, the ratio to zoom-in/-out, the distance to shift, the angle to rotate or the luminance parameter value of a light source of the digital microscope module. In addition, if the interactive application is a display mode switching, the method further comprising the steps of: switching a display mode to a single display mode, a parallel display mode, and an array mode to generate a single or simultaneous display or arrangement of the AR images of the same or different objects; and displaying the AR images to a display module configured as a head-mounted display (HMD), s stereo display or a flat display.

The non-transitory computer readable medium for storing the programs, the software, the algorithm, or the firmware loaded in the system for generating the augmented reality (AR) images is disclosed. The programs, the software, the algorithm, or the firmware stored on the non-transitory computer readable medium forms various modules for different functions in the system, comprising: the evaluating module, the alerting module, or the feedback or community module. Additionally, a plurality of applications for different purposes can be performed through the programs, the software, the algorithm, or the firmware stored on the non-transitory computer readable medium. The applications can be an interactive object observing system, a microsurgery training system, or an electronic component assembly training and examining system.

Alternatively, the processing module 11 of the present invention could also be a system-on-chip (SoC) system. The SoC system is configured as the processing module 11 of a system for generating the augmented reality (AR) images. The SoC system is configured to track and parse the user's motions to the observed object and generates a plurality of corresponding AR images when the interactive application is triggered. The SoC system is preferably coupled to a digital microscope having a vergence module 31 comprising a reflection mirror unit 311 and a camera unit 231-233. A microscopically observed object can be seen by the user when using the digital microscope and the SoC system. The camera unit 231-233 may capture one or more instant images of the observed object, and then transmit the instant images to the SoC system. The SoC system or the user's motions may adjust the corresponding or geometric relationship between the reflection mirror unit and the camera unit in response to control signals related to the user's motions. The control signals may also be generated by an automatic adjustment rule.

Figure 8A:
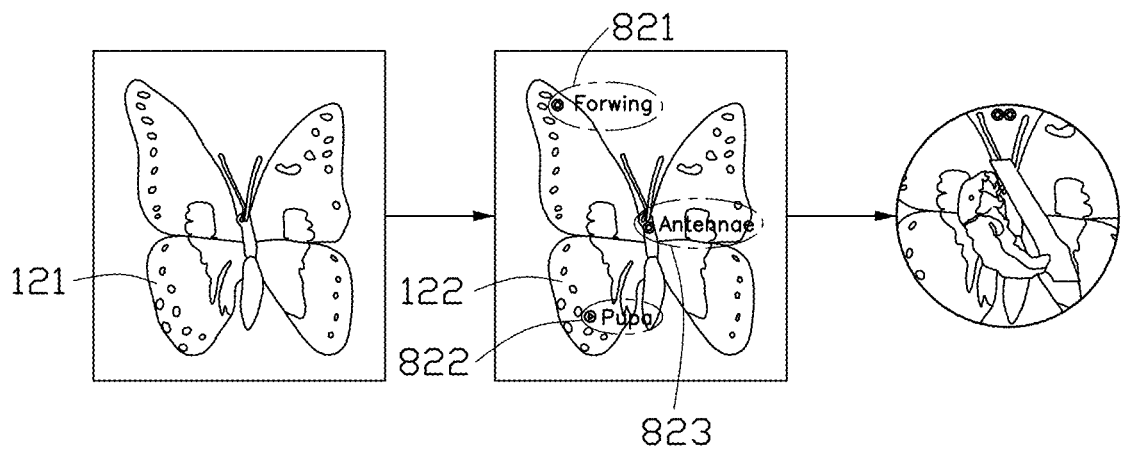
FIGS. 8A-8D are the schematic diagrams illustrating the AR images of the microsurgery training system embedded with a stereoscopic video see-through technique in accordance with the different preferred embodiments of the present invention.
Figure 8B:
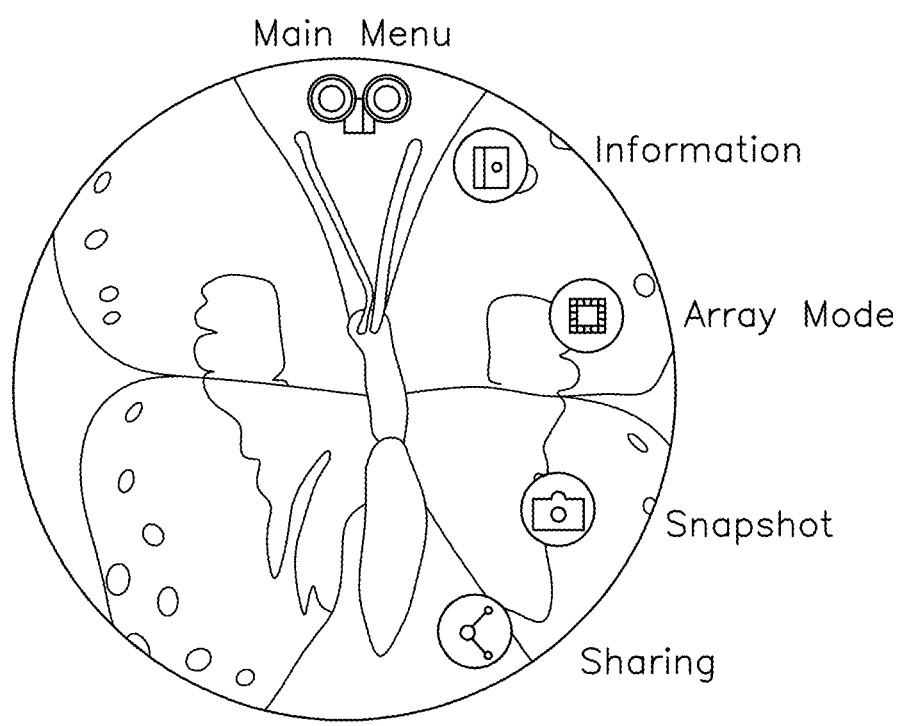
Figure 8C:
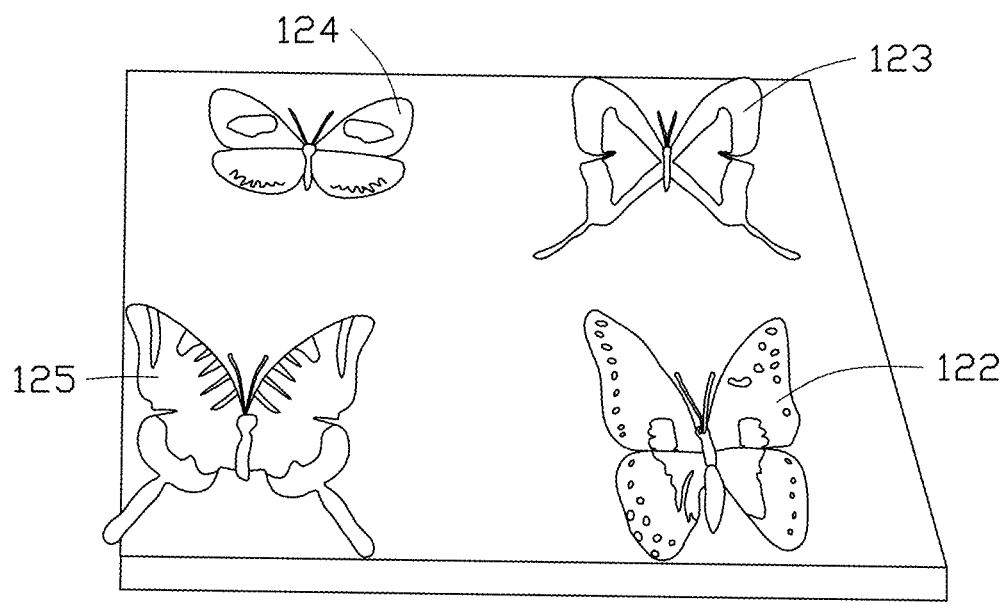

FIGS. 8A-8D are the schematic diagrams illustrating the AR images of an interactive object observing system embedded with a stereoscopic video see-through technique in accordance with different preferred embodiments of the present invention. The interactive object observing system is one of the various applications of the present invention and can be performed by the system described in FIGS. 1A and 1B. The purpose of the interactive object observing system is to provide an interactive experience for the user in a microscopic observation. The user can see the instant image of the observed object, and use a hand or the simulation tool to trigger the interactive application. The interactive object observing system is embedded with a stereoscopic video see-through technique that configured in the system for generating the augmented reality (AR) images, wherein the observed objects 121-125 are bodies or tissues of a tiny organism, a specimen, or a prosthesis. In FIGS. 8A and 8C the observed objects 121-125 are butterflies. The stereoscopic video see-through technique allows the digital microscope module 132 to capture the instant images during time period T1-T4 of the observed object 121-125 or the status of one of the operating or feature region 821-823. The processing module 11 may form, overlap and output the virtual object to a display module synchronously for diminishing the alignment error or reducing the latency, and then extend the application fields such as displaying the static image to the dynamic one. As shown in the central figure of FIG. 8A, the observed object overlapped with the corresponding icons comprising multiple functions: a manual mode, information mode, array display mode, snapshot, or sharing to the social networks. An arrangement of icons and the observed object 121-125 are shown in FIG. 8B. The "array mode" icon in FIG. 8B can be transformed into single display mode or parallel display mode by clicking or pressing the display mode switching object 65. The "information" icon can be triggered to generate additional texts, graphics, or videos regarding the observed object or the microsurgery. The "sharing" icon in FIG. 8B can be triggered to share a current operation of the system. The "snapshot" icon in FIG. 8B can be triggered for the camera unit to capture the instant image of the observed object or a current AR image.

Moreover, as shown in the right upper figure of FIG. 8A, a virtual object depicting a larvae of the butterfly is presented to the user by the display module. The virtual object of the larvae can be triggered by the user's motion, specifically the user's motion when interacting with the icons in the central figure of FIG. 8A and FIG. 8B. Accordingly, with the interactive object observing system of FIGS. 8A and 8B, the user can receive multimedia information such as texts, photos or videos while observing the samples without disruptions, and if one who is dissecting small animals, he/she can reach the atlas from the HMD by simply waving the knife or forceps in the corner. The interactive object observing system of FIGS. 8A and 8B can be performed with the evaluating module, the alerting module, or the feedback or community module. During the microsurgery training, the user's motion would be evaluated by the evaluating module to determine its' correctness. The evaluating module may also provide suggestions or guidance on the user's motions, such as suggested movement speed or route. Should one or more incorrect motions occurred, the alerting module would notify the user. The feedback or community module may upload a video or the AR images of the user's operation in the interactive object observing system.

Figure 8D:
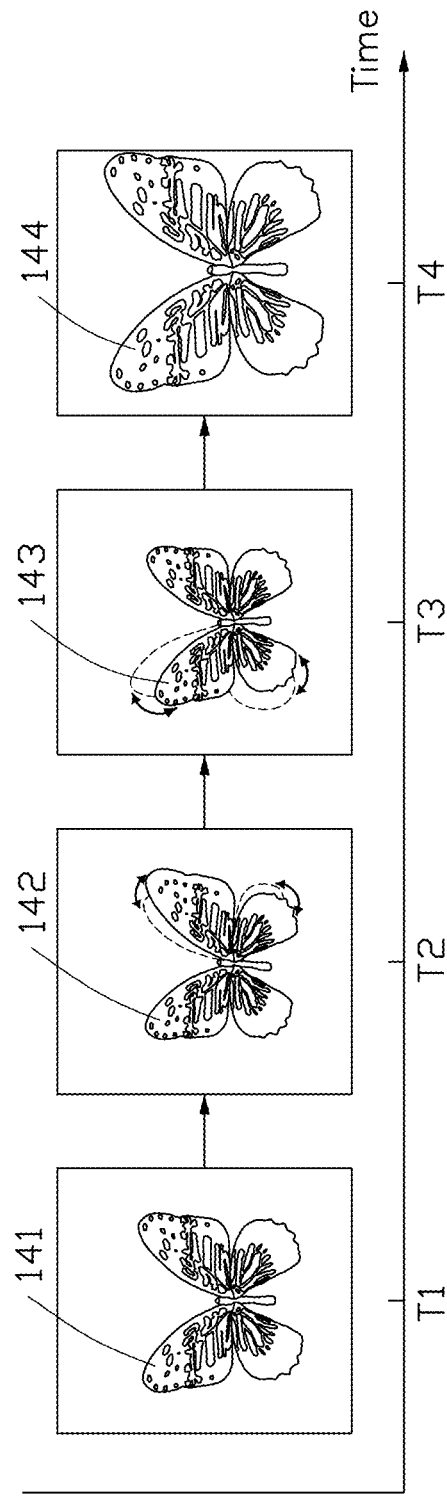

FIG. 8D is a schematic diagram illustrating the AR images of the interactive object observing system. The observed objects 141 in time period T1 is a butterfly specimen. In the time period T1, the system displays the instant image of a butterfly specimen 141. In time periods T2, T3, and T4, the system generates virtual objects 142-144 resembling the butterfly specimen 141, and the virtual objects 142-144 are animated. The virtual objects 142-144 overlap the butterfly 141 in the time periods T2-T4. In the time periods T2 and T3, the virtual objects 142 and 143 flap their wings, thus the user sees a vivid animation of the observed object 141. In the time period T4, the virtual object 144 flaps the wings and flies away. The virtual objects 142-144 are parts of the interactive application of the system, and presences of the virtual objects 142-144 can be triggered by the user's motion.

Figure 9A:
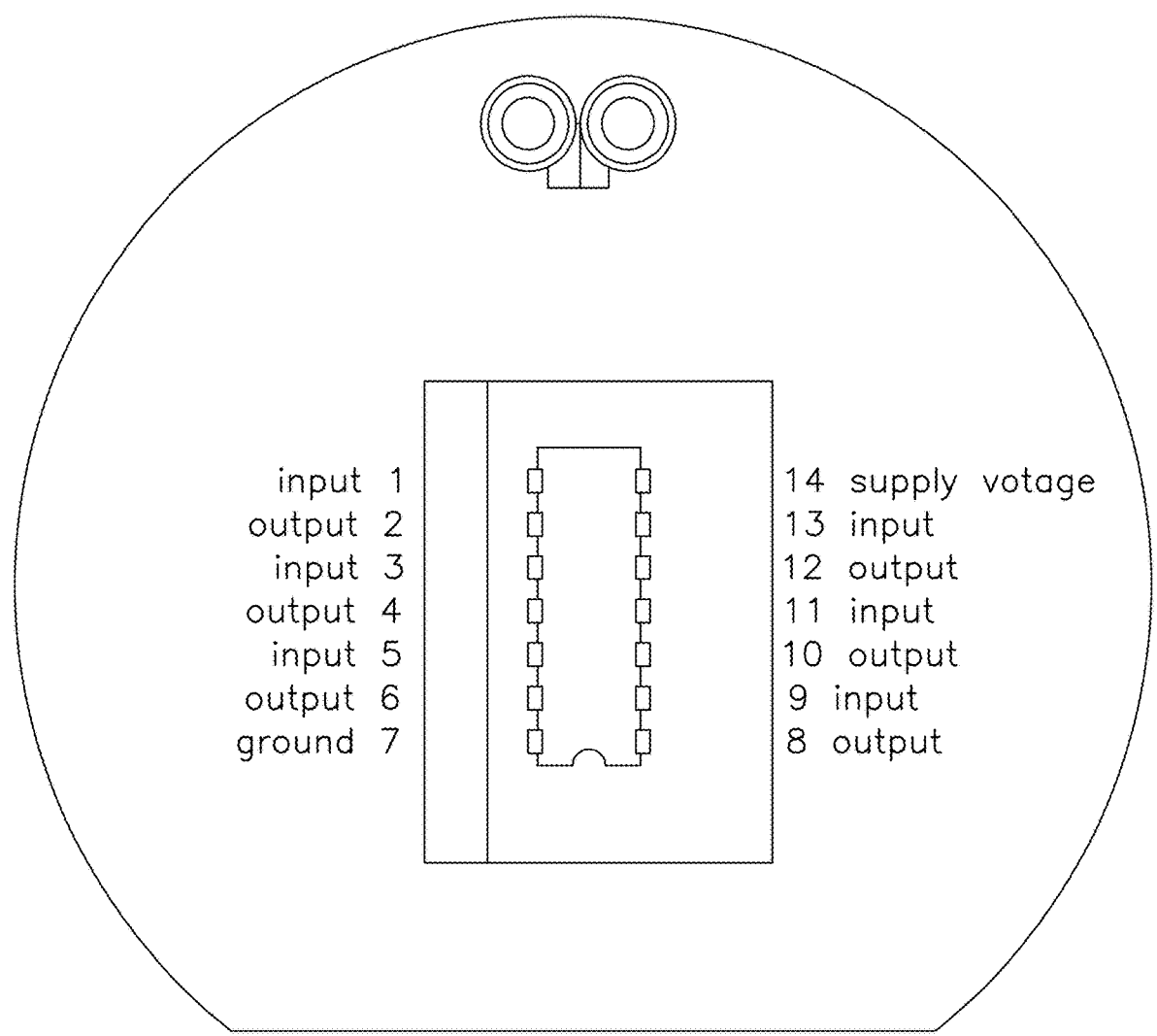
FIGS. 9A and 9B are the schematic diagrams illustrating the AR images of the electronic component assembly training and examining system embedded with a stereoscopic video see-through technique in accordance with the different preferred embodiments of the present invention.
Figure 9B:
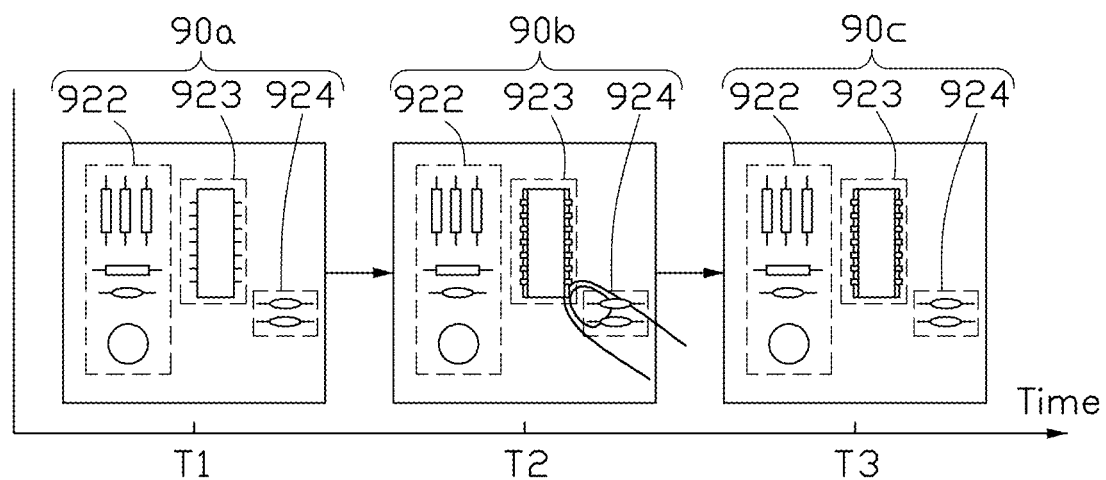

FIGS. 9A and 9B are the schematic diagrams illustrating the AR images of the electronic component assembly training and examining system embedded with a stereoscopic video see-through technique in accordance with different preferred embodiments of the present invention. The electronic component assembly training and examining system is one of the various applications of the present invention and can be performed by the system in FIGS. 1A and 1B. The purpose of the electronic component assembly training and examining system is to provide electronic component assembling training sessions to the user. The electronic component assembly training and examining system is an application of the present invention and can be a software, a firmware, a program, or an algorithm stored in the non-transitory computer readable medium coupled to or in the processing module 11. As shown in FIG. 9B, the observed objects 90a-90c are printed circuit boards (PCBs). Electronic components can be installed or fixed on the PCB in FIG. 9B, such as a resistor, a medium, or a capacitor. The stereoscopic video see-through technique can be that the digital microscope module captures the instant images of the observed object or the status of one of an operating or feature regions 922-924 for the processing module 11 from time periods T1-T3 to form, overlap and output the virtual object to a display module synchronously during the time periods T1-T3 for diminishing the alignment error or reducing the latency. In the time period T1, the feature region 922 is installed with multiple electronic components, the operating region 923 is a designated installation site for a chip, and the feature region 924 has several virtual objects indicating a presumable configuration of electronic elements on the PCB 90a. In the time period T2, the user installs the chip onto the operating region 923, and the virtual objects on the feature region 924 overlap the instant image of the user's finger. In the time period T3, the user's finger leaves the PCB 90c and the virtual objects on the feature region 924 is still present. In other words, the virtual objects of all of the layout of electronic element to be fixed or assembled are visible at the beginning of the assembly or training process, and they are removed, changed to transparent or disabled with a real-time tutorial or sharing and the related AR images with/without the virtual object temporarily and automatically for preventing the interference in response to a temporary disable mechanism. The evaluating module 78 in FIG. 7 may assess a correctness of the user's motion, namely the correctness of chip installation, in the time period T2 or T3: the evaluating module 78 compares the user's motions and a preset installation site of the chip, generates an evaluation result to indicate the correctness of the installation, and provides response to the user based on the correctness. The alerting module 79 in FIG. 7 may visualize the response generated by the evaluating module 78. A green signal indicating a correct installation or a red signal indicating an incorrect installation can be displayed to the user.

As shown in FIG. 9A, the observed object is an IC having the pins for transmitting and receiving different data or signals, and thus it's not required for the user to leave away or to be interrupted frequently for the purposes such as seeking the data or parameter value in the user manual according to the present invention.

Figure 10A:
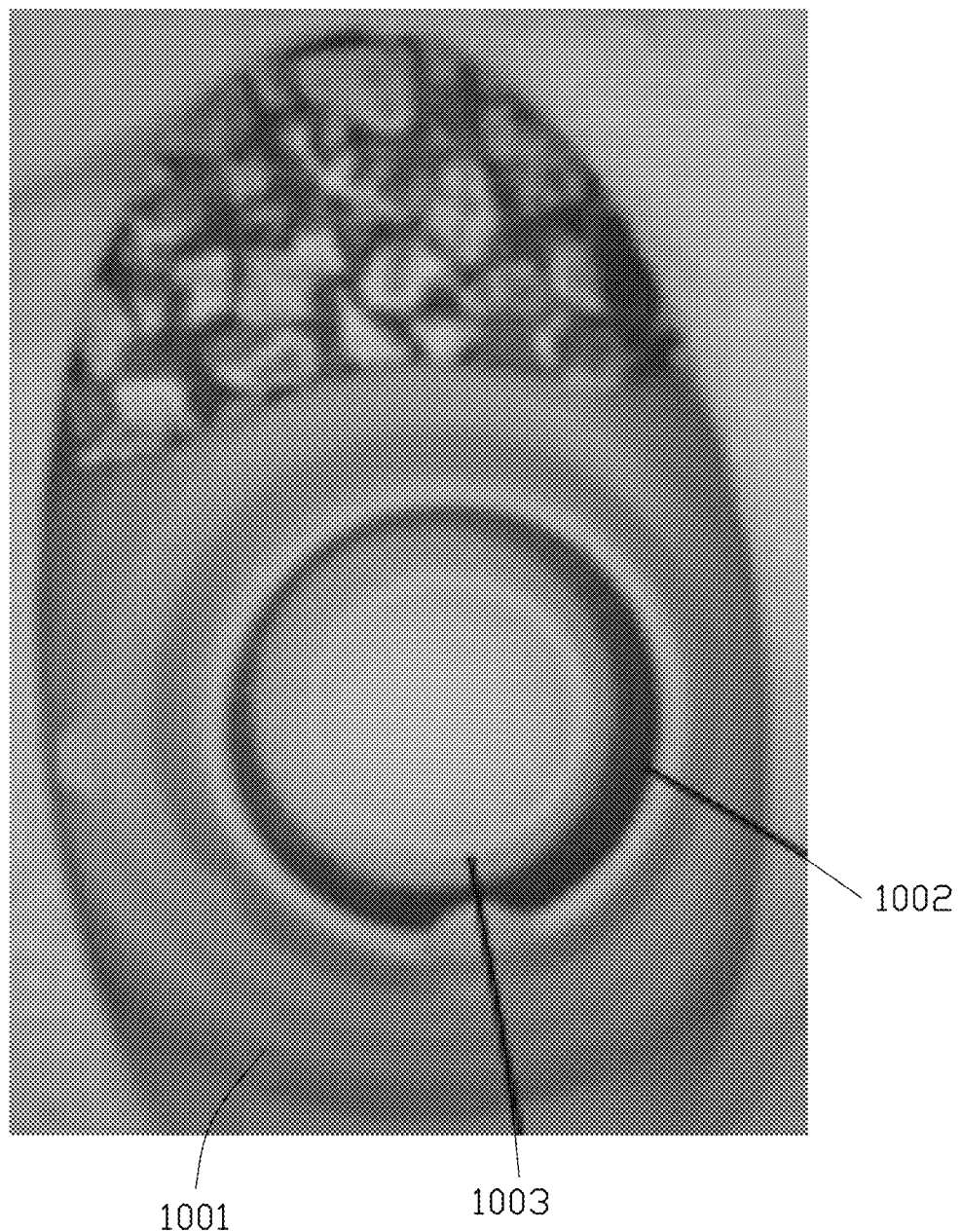
FIGS. 10A and 10B are the schematic diagrams illustrating the AR images of the microsurgery training system embedded with a stereoscopic video see-through technique in accordance with the different preferred embodiments of the present invention.
Figure 10B:
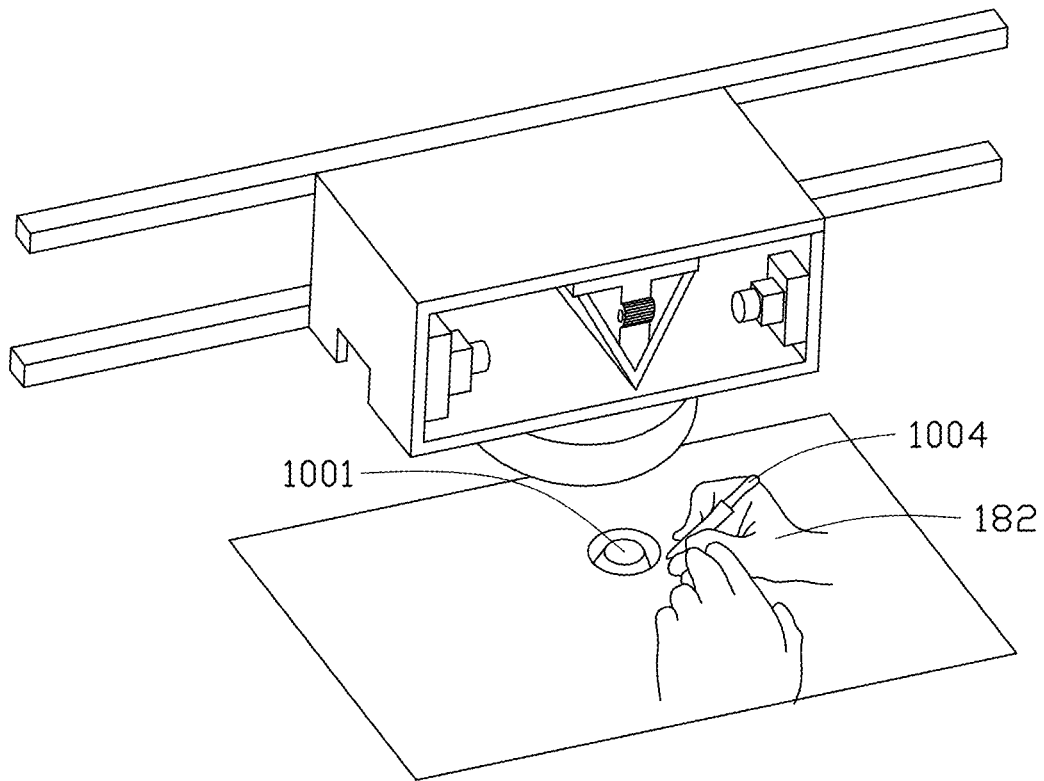

FIGS. 10A and 10B are the schematic diagrams illustrating the AR images of the microsurgery training system embedded with a stereoscopic video see-through technique in accordance with different preferred embodiments of the present invention. The microsurgery training system is one of the various applications of the present invention and can be performed by the system in FIGS. 1A and 1B. The purpose of the microsurgery training system is to provide microsurgery training sessions for the user to practice microsurgery procedures with the digital microscope module and the processing module 11 of the system. The microsurgery training system is an application of the present invention and can be a software, a firmware, a program, or an algorithm stored in the non-transitory computer medium coupled to or in the processing module 11 of the system. The microsurgery training system in FIGS. 10A and 10B provide a training environment for the user to practice microsurgery procedures. The types of the microsurgery include but not limited to the surgical procedures on Cataract, Retina, Mccula and Cornea. Tools or instruments for above surgery procedures may comprise a capsulorhexis forceps 1004, and the observed object in the surgical procedure can be the real body or tissues of a tiny organism, a specimen or a prosthesis. The stereoscopic video see-through technique is the technique that the digital microscope module captures the instant images of the observed object such as an artificial eye model 1001 or the status of one of the operating or feature region 1002. The processing module 11 forms, overlaps, and outputs a virtual object 1003 as a capsulorhexis maker or real-time guidance for the surgery to a display module synchronously, for diminishing the alignment error or reducing the latency. Moreover, the user can use a probe or a real surgery instrument during the microsurgery training. Besides, the microsurgery training system can be used to perform the method for generating the augmented reality (AR) images of an observed object of the present invention as well.

The foregoing description, for purpose of explanation, has been described with reference to specific embodiments. However, the illustrative discussions above are not intended to be exhaustive or to limit the present application to the precise forms disclosed. Many modifications and variations are possible in view of the above teachings. The embodiments were chosen and described in order to best explain the principles of the present application and its practical applications, to thereby enable others skilled in the art to best utilize the present application and various embodiments with various modifications as are suited to the particular use contemplated.

While particular embodiments are described above, it will be understood it is not intended to limit the present application to these particular embodiments. On the contrary, the present application includes alternatives, modifications, and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

Although some of the various drawings illustrate a number of logical stages in a particular order, stages that do not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

What is claimed is:

1. A system for generating an augmented reality (AR) image, the system comprising:
    a processing module configured to track and parse user's motions to an observed object and correspondingly generate the AR image when an interactive application is triggered; and
    a digital microscope module coupled to the processing module and comprising a vergence module having a reflection mirror unit and a plurality of camera units;
    wherein the camera units capture at least one instant image of the observed object and then transmit the instant image to the processing module, and the reflection mirror unit is operatively regulated to adjust a corresponding or geometric relationship between the reflection mirror unit and the camera units, in response to control signals related to the user's motions.

2. The system of claim 1, further comprising a single-chip microcontroller interface module coupled to the processing module for activating the digital microscope module in response to the control signals.

3. The system of claim 2, further comprising a positioning module coupled to the digital microscope module, wherein the vergence module further comprises a vergence controller unit for moving the reflection mirror unit in an operable space in response to the control signals, and the user's motions entering into or departing from the operable space for approaching, touching, leaving, operating, installing or fixing the observed object and/or changing a status of an operating region or a feature region.

4. The system of claim 1, further comprising an operable interface module coupled to the processing module for selecting or performing the user's motions by the user, and/or configured to have an operating parameter adjustment object and/or a display mode switching object.

5. The system of claim 4, wherein the operating parameter adjustment object is configured to provide focus adjustments, zoom-in/-out, shift distances, angles of rotation, or light adjustments, and the display mode switching object is configured to provide a selection of display mode for the AR image and comprises a single display mode, a parallel display mode, and an array mode.

6. The system of claim 1, wherein the interactive application comprises switching display modes for the observed object, activating a real-time tutorial, or sharing a current operation.

7. The system of claim 1, wherein the AR image comprises a user interface (UI), icons, objects, video, and/or information related to the interactive application.

8. The system of claim 1, wherein the AR image comprises a virtual object overlapping with the instant image.

9. A system for generating an augmented reality (AR) image, the system comprising:
    a processing module configured to track and parse user's motions, to correspondingly generate control signals, receive instant images having at least one object or a status of at least one of an operating region and a feature region in response to a user's motions or control signals, process the instant images to generate at least one virtual object of the AR image; and a digital microscope module coupled to the processing module, and comprising a vergence module having a reflection mirror unit and a plurality of camera units, wherein the reflection mirror unit is operatively regulated.

10. The system of claim 9, wherein the AR image comprises the virtual object overlapping with the instant image.

11. A method for generating an augmented reality (AR) image of an observed object, comprising the steps of:

tracking and parsing a user's motions to correspondingly generate a plurality of control signals;

generating and processing instant images of the observed object to form at least one virtual object;

adjusting a corresponding or geometric relationship between a reflection mirror unit and a plurality of camera units by regulating the reflection mirror unit in response to the control signals related to the user's motions; and generating the AR image composed of user interface (UI), icons, objects, video, information related to an interactive application, or the virtual object.

12. The method of claim 11, wherein the step of tracking and parsing the user's motions further comprises:

operating a positioning module, a simulation tool, a user's hand or finger, a surgical instrument, or experimental instrument to enter into an operable space, depart from the operable space, approach the observed object, touch the observed object, move away from the observed object, operate the observed object, install the observed object, fix the observed object, and/or change a status of an operating region or a feature region;

removing the virtual object, transparentizing the virtual object, disabling a real-time tutorial, or stopping a sharing of current operation; and adjusting a focus, a ratio to zoom-in/-out, a shifting distance, angle of rotations, or light adjustments of a digital microscope module.

13. The method of claim 11, wherein the interactive application is utilized to switch a display mode, and the method further comprising the steps of:

switching the display mode to a single, a parallel, or an array mode to generate a single or simultaneous display arrangement of the AR image of the observed objects; and displaying the AR image to a display module configured as a head-mounted display (HMD), a stereo display, or a flat display.

14. The method of claim 13, wherein the step of tracking and parsing the user's motions comprises:

triggering the interactive application to switch the display mode for the observed object, activate a real-time tutorial, or share a current operation.

15. A digital microscope module, coupled or connected to a processing module of a system for generating an augmented reality (AR) image, the digital microscope module comprising:

a plurality of camera units for receiving instant images of at least one object or a status of at least one of an operating region and a feature region; and a vergence module comprising a reflection mirror unit to reflect the instant images of the object, the operating region, or the feature region to the camera units, wherein the reflection mirror unit is operatively regulated to adjust a corresponding or geometric relationship between the reflection mirror unit and the camera units.

16. The digital microscope module of claim 15, wherein the vergence module further comprises a first beam splitting element to split incident light.

17. The digital microscope module of claim 15, further comprising a second beam splitting element to receive reflected light from the vergence module.

* * * * *